United States Patent [19]

Stroh et al.

[11] Patent Number: 4,646,733
[45] Date of Patent: Mar. 3, 1987

[54] ENDOTRACHEAL TUBE FOR A HIGH-FREQUENCY RESPIRATOR

[75] Inventors: Norbert Stroh, Magstadt; Paul P. Lunkenheimer, Münster, both of Fed. Rep. of Germany

[73] Assignee: Firma Carl Freudenberg, Weinheim/Bergstr, Fed. Rep. of Germany

[21] Appl. No.: 781,794

[22] Filed: Sep. 30, 1985

[30] Foreign Application Priority Data

Sep. 29, 1984 [DE] Fed. Rep. of Germany ....... 3435849

[51] Int. Cl.[4] ............................................. A61M 16/00
[52] U.S. Cl. .......................... 128/207.16; 128/204.25; 128/207.14; 128/207.15; 128/205.24; 128/204.21
[58] Field of Search ....................... 128/204.25, 205.24, 128/207.16, 207.14, 207.15, 204.21

[56] References Cited

U.S. PATENT DOCUMENTS

| | | | |
|---|---|---|---|
| 4,171,697 | 10/1979 | Arlon | 128/204.25 |
| 4,488,548 | 12/1984 | Agdanowski | 128/204.25 |
| 4,508,117 | 4/1985 | Rodari | 128/205.24 |
| 4,519,388 | 5/1985 | Schwanbam et al. | 128/204.25 |

FOREIGN PATENT DOCUMENTS

812296  3/1981  U.S.S.R. .......................... 128/207.14

Primary Examiner—Henry J. Recla
Attorney, Agent, or Firm—Felfe & Lynch

[57] ABSTRACT

An apparatus for the high-frequency artificial respiration of living animals or human beings has a flexible endotracheal tube for introduction into the trachea thereof. The flexible endotracheal tube has an outlet end, a valve at the outlet end and control and air supplies along the endotracheal tube to the valve. The control operates the valve to produce steep-flanked respiratory-air pulses. The valve can serve simultaneously for removing used air through a conventional endotracheal tube as a sleeve about the other endotracheal tube.

24 Claims, 11 Drawing Figures

ENDOTRACHEAL TUBE FOR A HIGH-FREQUENCY RESPIRATOR

The invention relates to a high-frequency respirator and, more particularly, an endotracheal tube therefor.

An introduction to the field of high-frequency respirators, references to additional literature thereon, and some description thereof is given in *Medizintechnik Produktinformation* (Health Equipment Information) of Draegerwerk AG in the section entitled "Hochfrequenzbeatmung" ("High-Frequency Respiration"), December 1983, No. 119, bibliographic identification ISSN 0261-0736.

The inventors have found several different kinds of high-frequency respirators (HFPV, HFO, HFJV, etc.) work best when the high-frequency respiratory-air pulses they produce for respiration are sharp-cornered, i.e., have very steep rise and fall flanks. Setting out from this knowledge, known high-frequency respirators generally have the following disadvantages:

(a) The high-frequency air-pulse producer which produces the high-frequency respiratory-air pulses of the respirator is at a distance from the point at which the respiratory-air pulses emerge from the respirator into the trachea for the respiration which is on the order of a meter. The travel over this distance from the producer to the outlet where the respiratory-air pulses emerge into the trachea for the respiration slurs the respiratory-air pulses.

(b) A feed line for carrying the air pulses from the producer to an endotracheal tube having the outlet for the respiratory-air pulses has a cross-sectional diameter of around 1–2 mm. One end of this feed line is cemented to the endotracheal tube to communicate with a line in the wall of the endotracheal tube which must, therefore, be narrower than the wall thickness of the endotracheal tube. In the state of the art, the line in the endotracheal tube has a cross section of 0.7 mm wide by 1 mm, for example. The respiratory-air pulses are also slurred by the high air resistances of these small cross section lines. Indeed, the cross section of the line in the endotracheal tube may not even be the narrowest point. Instead, the adhesive at the transition from the feed line to the endotracheal-tube line may further narrow the line cross section at that point.

(c) Both the feed and endotracheal lines are made of a plastic which is soft for another, known purpose. In many sections, the walls of these lines are not even a tenth of a millimeter thick and, therefore, yield to the pressure of the air and, thus, slur the respiratory-air pulses even more.

(d) The frequencies of the high-frequency respiratory-air pulses are around 1 to 50 Hz. The higher the frequency, the more the respiratory-air pulses are slurred as a function of the frequency. For many applications, however, higher frequencies are otherwise better. The respirators in state of the art do not permit higher respiratory-air pulse frequencies, however, for there is no benefit in producing higher air-pulse frequencies if virtually naught but a steady flow emerges from the outlet of the endotracheal tube as respiratory-air pulses.

(e) The narrowest cross section in a line determines its resistance to flow. In the respirators of the state of the art as above mentioned, very thin lines are used which, therefore, have a high resistance to flow. Nevertheless, sufficient air for artificial respiration must be made available at the outlet of the endotracheal tube. This can be achieved, therefore, in no way but by raising the pressure of the air pulses to the limit. Thus, the respiratory-air pulses emerge at the outlet of the endotracheal tube with extremely high velocity and then, of course, hit the trachea or trunk bronchi with a high thrust. The latter are, therefore, physiologically stressed at the place of impact, because, there, the surface mucus is blown away, the heat balance is no longer correct, the moisture balance is no longer correct, etc.

It is, therefore, the object of the invention to prevent the slurring of the respiratory-air pulses in a simple manner.

According to the invention, this is accomplished with an endotracheal tube for a high-frequency respirator having a proximal end adapted to extend from a breathing passage of a patient and a distal end adapted to extend into the trachea of the patient. The distal end defines an outlet having a valve with an inlet communicating with the interior of the endotracheal tube and outlet structure for directing respiratory air pulses into the trachea of the patient, whereby the air pulses produced are not slurred by passage to the outlet end of the endotracheal tube for emission as the respiratory-air pulses. A respiratory air supply structure is at the proximal end of the endotracheal tube for supplying respiratory air for the respiratory-air pulses from the valve and control structure passes along the endotracheal tube to the valve from the distal end of the tube for operating the valve to produce the respiratory-air pulse of the supplied respiratory air.

Each respiratory-air pulse is, therefore, available with steep flanks at the outlet of the artificial-respiration, endotracheal-tube air line and is, therefore, of especially great effectiveness. It makes it possible, for example, to bring certain parts of a lung into resonance for quite novel effects in the field of high-frequency artificial respiration.

Another advantage of the invention is that, basically, artificial respiration independent of the compliance of the lungs can be achieved. The alveolar ventilation of a lung segment then depends only on the frequency and radiation characteristics of the flow pulse.

Very compact, mechanical valves can be made and used in the invention. If the valve is electrically operated, however, a control cable that lies still can be used, whereas, in the case of a mechanical valve, the control cable must, of course, move.

If a mechanical rotary slide valve is used, however, the mechanical control cable only needs to rotate. This provides simpler, mechanical-valve actuation for this application than, e.g., a reciprocated control cable, which, even if it can well withstand tension, is easily deflected under pressure. If the mechanical rotary slide valve is flat, it can be so oriented across the endotracheal tube and, thus, made short in the axial direction of the tube. Accordingly, the flexibility of the outlet end of the tube is not too greatly affected by the valve. A flat slide valve also has short ports which contribute to making the respiratory-air pulses steep-flanked. Moreover, the rotor of a flat, rotary slide valve has little rotating mass, so that imbalances are unimportant. The little mass of the rotor of a flat, rotary slide valve also means that it immediately follows any change in the rotary speed of the mechanical control cable. A gear on a flexible, rotating control cable could engage the outer circumference of the rotor of a rotary slide valve. Then, however, a reduction is needed between the circumference of the rotor and that of the gear driven by the control cable. This is avoided by concentric, direct drive of the rotor.

If the endotracheal tube of the invention is thin enough, a previously-known, conventional endotracheal tube can be used, unaltered, as a sleeve surrounding the former; one need only insert the tube according to the invention into it. This even makes it possible to change over from high-frequency artificial respiration via the invention to the proper, previous use of the previously-known, conventional endotracheal tube during treatment simply by withdrawing the tube according to the invention out of the previously-known, conventional endotracheal tube. The control structure, the endotracheal-tube, artificial-respiration air-supply line and the valve of the invention then form one structural unit which can be made, stored and used by itself or with the previously-known, conventional endotracheal tube. In addition, if the unit of the invention is thin enough relative to the previously-known, conventional endotracheal tube used as a sleeve thereabout, the artificial respiration air can flow back in the space therebetween which can have a large flow cross section although, likewise, the large cross section is also available for the delivery of the artificial respiration air.

The pulse level (amplitude) and also the pulse-flank steepness can be further improved by providing a negative flow resistance, e.g., a pressure-raising apparatus, immediately ahead of the valve in the direction of flow from the outlet, i.e. on the opposite side of the valve from the outlet end of the tube.

One suitable pressure-raising apparatus is a turbine. It requires only rotary delivery of energy which, as for the rotary valve control, is simpler than a reciprocating delivery. One might provide two flexible cables or shafts, one for controlling the valve and the other for driving the air turbine device. However, one flexible shaft can serve for both. Indeed, rotary slide valves which also function as a turbine are known and can be used. No additional, separate air turbine device is then needed.

If a rotary valve having more than one opening around its circumference is used, high respiratory-air pulse frequencies are achieved even though the shaft rotating the valve is rotating at a fraction of these frequencies.

A Y-shaped, tubular divider may be attached to the outlet end of endotracheal tube of the invention by the base of the Y shape of the tubular divider. With this, the sharp-cornered, respiratory-air pulses not only reach the branching, trunk bronchi to respective lungs, but even are directed into these trunk bronchi. One is thus sure that the respiratory-air pulses do not impact upon the inside wall of the trachea or the trunk bronchi, but are, instead propagated along the trunk bronchi.

If the above-described rotor of a rotary slide valve is axially enveloped, i.e., sandwiched, by portions of a stator, and does not project beyond the circumference of the stator portions, the rotor cannot lie against any part of the trachea or trunk bronchi and thus be impeded in its rotation or cause injury by its rotation.

Instead of the above-described, Y-shaped, tubular divider, a stator which also circumferentially envelopes the rotor can have two exit openings operated by the rotor 180° apart and in the plane, i.e. circumferential of the endotracheal tube. These openings aim the respiratory-air pulses which emerge therefrom at least approximately into the two trunk bronchi.

The endotracheal tube can provide artificial respiration with a positive average pressure. Due to this pressure, exhaled air flows in the annular gap thereabout, with or without the conventional endotracheal tube as a sleeve, into the open air. The disadvantage of conventional artificial respiration at elevated pressure for the required rate of flow of air which, in the case of high air needs, reaches levels that can no longer be tolerated physiologically, can be compensated by a suction line. This suction line is connected outside of the mouth to the annular gap between the conventional endotracheal tube as a sleeve and the endotracheal tube for artificial respiration as described. The breathing air flowing out can be actively and definitely aspirated in this way. The average breathing pressure can be adjusted through the level of the suction and the rate of flow of the air delivered for the respiratory-air pulses.

The described artificial respiration apparatus, although of small size, is suitable for aerosol and powder insufflation. For this, preferably, the valve producing the respiratory-air pulses at the lungward, outlet end of the endotracheal tube is adapted for additional function as an atomizer. Aerosol insufflation is useful for pulmonary parenchymal mobilization, i.e., mucus mobilization, which can be strictly localized. Powder insufflation is useful for bronchography, the powder being used as a contrast agent. Coagulation promotion can also be achieved in these ways.

In the best mode, the valve has two openings or discharge ports respectively on opposite sides of the axis of the endotracheal tube for emitting the respiratory-air pulses at an angle with it or an imaginary prolongation of approximately 30°. This relationship corresponds approximately to that of the trunk bronchi with respect to the trachea and, thus, assures better artificial respiration. Relative rotation from the trunk bronchi must be avoided, of course, and, therefore, it has been found desirable to identify the position of at least one of the discharge portions with a marking extending along the entire length of the endotracheal tube.

The valve can be provided with at least one reverse blast opening adjacent the discharge port. It directs air in the direction of the return air flow, away from the outlet end of the endotracheal tube facing the lung in use. When a sharp air blast issues from the reverse blast opening, therefore, a kind of Venturi or entrainment effect is thus produced which makes it possible to remove waste breathing air from the lung. The effect is particularly effective when the valve opens the discharge ports and reverse blast openings at different times and, especially, alternately. The common opening system of the valve is therefore advantageous.

Each discharge port and/or the reverse blast opening can be provided with a throttle. It has been found desirable for the throttle to be such that, by its actuation, the ratio of the air streams passing through the discharge ports and the reverse blast openings can be adjusted in a mutual relationship. The specific conditions during the pressure and suction phases can thus easily be adapted to the individual requirements of the patient.

The endotracheal tube of the invention and the conventional endotracheal tube which may be used as a sleeve thereabout can be attached to one another or made in one piece. Both assure optimum flow conditions in the vicinity of the valve. A coaxial relationship between the endotracheal tube of the invention and the endotracheal-tube sleeve is also advantageous and achievable in this way. However, an eccentric relationship therebetween results in easier flexibility in one direction which may facilitate proper insertion of the apparatus into the trachea.

The endotracheal tube of the invention and the conventional endotracheal-tube sleeve can also be independent of one another. This makes it possible first to insert the conventional endotracheal tube into the trachea and then introduce the endotracheal tube of the invention thereinto. The insertion and removal of the endotracheal tube of the invention is, in this case, greatly facilitated and, thereby, the transition from artificial respiration with the invention to natural breathing. Critical convalescent care can, in this manner, be largely avoided.

The reverse blast openings should be associated with the outside of the endotracheal tube in a very precise manner to obtain a good suction effect. The use of guides has proven advantageous from this point of view.

The apparatus according to the invention permits intensive artificial respiration with a frequency of 3/min. to 150/sec. and, thus, over the entire frequency range in question. The apparatus is sample to apply and in no way interferes with the return of spontaneous breathing during the treatment. It also can control the formation of secretions in the lung substantially better than heretofore.

The invention will now be described with the aid of embodiments shown in the drawings wherein.

In many animals, including humans, the trachea diametrically divides into two, right and left, for example, trunk bronchi. Typically, the right trunk bronchus branches off at a more obtuse angle than the left trunk bronchus and is also a little shorter. The right and left trunk bronchi respectively lead into right and left lungs which have various lobes in a manner known for each lung. The lobes are individual parts of the lung organ which respond quite differently to different frequencies of artificial respiration. In particular, the different lobes have different resonance frequencies, the actual resonance frequency of each depending on the age of the lung, injuries, etc. Thus, even if one lung lobe is respirated at or near resonance, another can be nevertheless far away from resonance. It is therefore necessary to be able to vary the frequency of respiration for diagnostic or therapeutic purposes.

The trunk bronchi branch out repeatedly (12 to 15 times) away from the trachea, so that one speaks also of the bronchial tree. The lumen which is available for an air stream from the trachea thus enlarges to the periphery of the bronchial tree, approximately exponentially. Because the respiratory-air pulses are produced with the invention approximately at the branching point of the trachea into the trunk bronchi, it is important to produce steep-flanked respiratory-air pulses at that point because the expansion of the lumen and the rest of the structure of the lung slur the flanks of the respiratory-air pulses therefrom.

Figures 1, 2, 5:
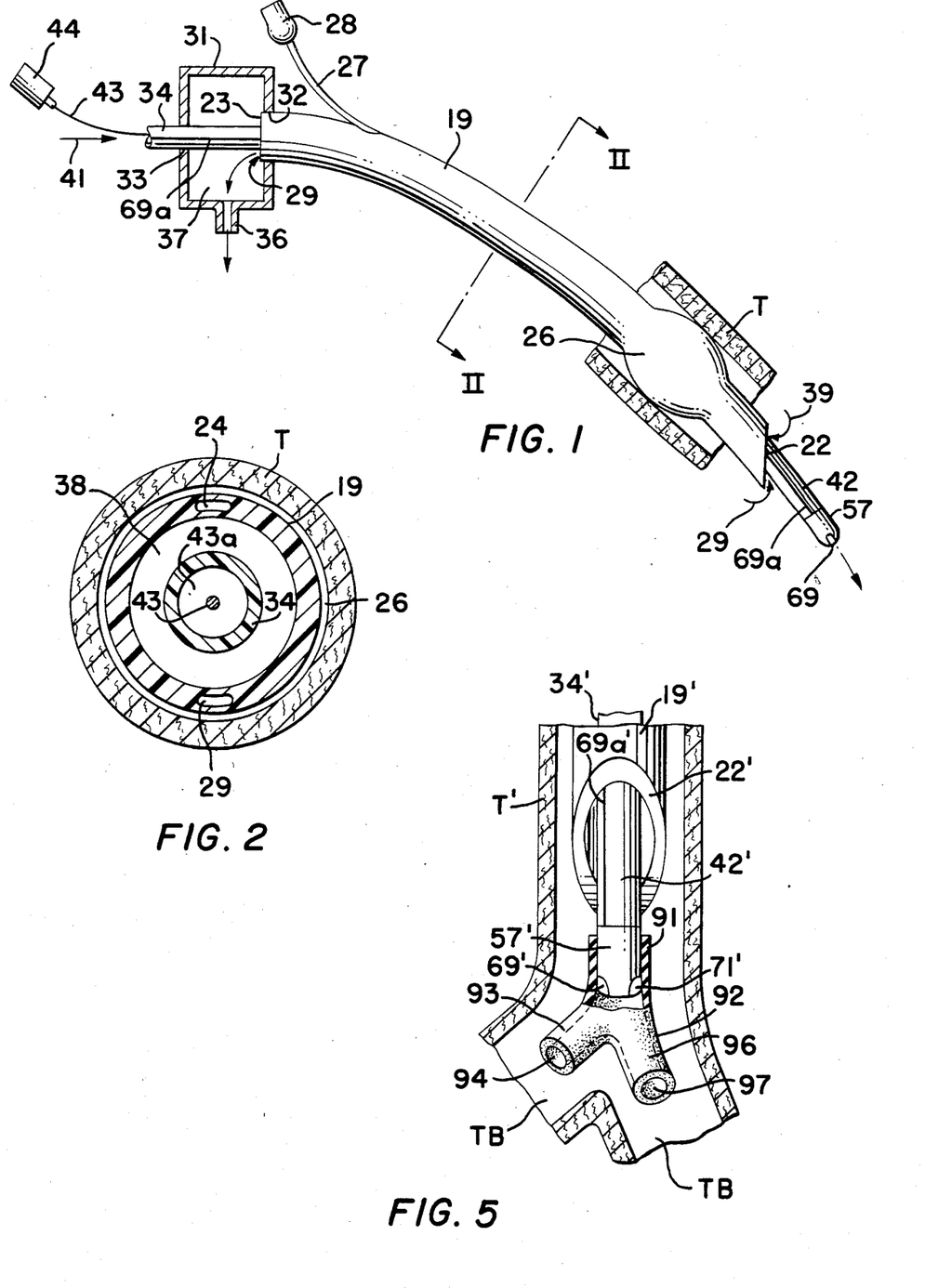
FIG. 1 is a perspective view of a portion of one embodiment in an operative environment therefor, partly broken away and in section.
FIG. 2 is an enlarged cross section of the embodiment shown in FIG. 1.
FIG. 5 is a front elevation of a portion of another embodiment, partly in section, in an operative environment in section.

For this, FIG. 1 shows a known, curved, conventional endotracheal tube 19. As usual, it is made from a transparent PVC hose having a slanting bottom end 22 for easier introduction into a trachea T, an opposite, radial end 23, an outside diameter of 11.5 mm, and a wall thickness of about 1.4 mm.

As shown in FIGS. 1 and 2, a passage or line 24 in the wall of the conventional endotracheal tube 19 communicates from an inflatable bulb 26 into a connecting line 27 which is cemented to the line 24 in the usual manner and passes into a coupling 28. The coupling 28 can be slipped over a pressure producer (not shown) for inflating the bulb 26 so that it can sealingly engage the inside wall of the trachea.

There is also another passage or line 29 in the wall of the conventional endotracheal tube 19. It is of a common type which extends along the length of the tube between its ends to serve for the aspiration of secretions or the like.

For this, and for further aspiration to be described, the radial top end 23 of the conventional endotracheal tube 19 is received, airtight, in an opening 32 of a socket head 31. A coaxially opposite opening 33 in the socket head has an airtight grip on another endotracheal tube 34, to be described, which is coaxial with the tube 19 and, therefore, passes through the socket head. A connection 36 on the socket head for an aspirator (not shown) aspirates from the cavity 37 of the socket head and, hence, also from the passage 29 as well as a passage 38 between the walls of the endotracheal tubes 19 and 34, the waste air entering the passage 38 at the bottom, lung end 22 of the conventional endotracheal tube 19 as indicated by the arrow 39.

Artificial respiration air is fed from a source (not shown) into an end of the endotracheal tube 34 at the socket head as indicated by arrow 41. The artificial respiration air from the source is not pulsed. It is necessary, under all circumstances, to prevent it from having a negative pressure with respect to the pressure of the ambient air, because this would result in immediate blockage of the lung. It is best for the artificial respiration air to have a pressure of a few millibars above the ambient air so that the lung will be inflated in any case.

The endotracheal tube 34 consists of a transparent, PVC, plastic hose. Its outside diameter is 7 mm and its inside diameter is 5 mm. Its end portion extending out of the socket head 31 for connection to the source (not shown) of artificial respiration air has already been described. As FIG. 1 shows, the opposite end portion 42 of the endotracheal tube 34 protrudes slightly out of the bottom, lung end 22 of the conventional endotracheal tube 19.

Inside the endotracheal tube 34 is a flexible shaft 43 of stainless steel having a diameter of 1.2 mm. It is solid, i.e., it is not made of spirally wound wire, to transfer considerable torque, but flexible enough to follow the entire curve shown in FIG. 1. In contrast to spirally wound flexible shafts which must be driven in rotation in the direction which increases the tightness of the spiral, too, there is no need with the solid shaft 43 to pay heed to the direction of rotation. Moreover, the non-wound, solid shaft 43 occupies less space than a wound shaft, so that a space 43a of extraordinarily large cross section is left for the artificial respiration air between the endotracheal tube 34 and the flexible shaft 43.

The shaft 43 is driven directly by an electric motor 44 as shown in FIG. 1. The speed of the motor can be regulated over a range between 600 and 2000 rpm. The motor 44 can be already installed inside the source (not shown) of the artificial respiration air so that the flexible shaft is inside of the endotracheal tube 34 from the outset or else the flexible shaft 43 can be carried by an air-tight seal (not shown) into the endotracheal tube 34.

Figure 3:
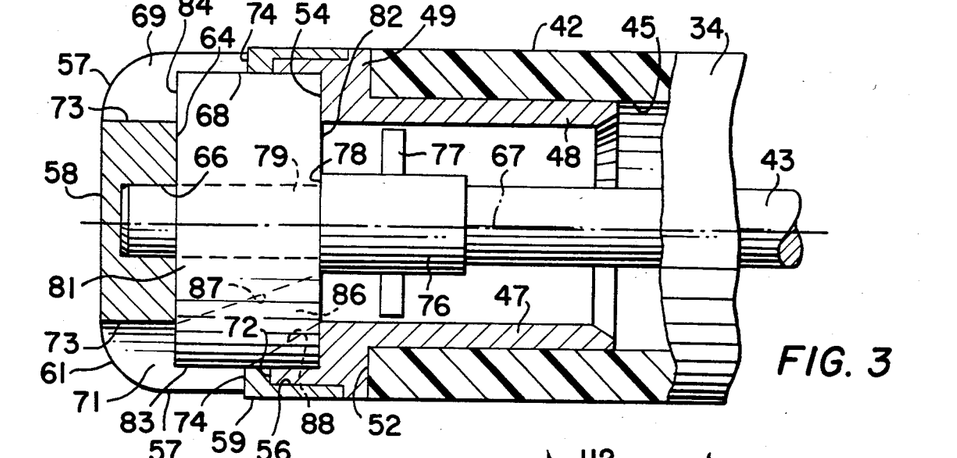
FIG. 3 is an enlarged longitudinal front elevation of an end portion of the embodiment shown in FIG. 1, partly in section.

As shown in FIG. 3, a nipple 48 of a casing is coaxially inserted into the projecting end 42 of the endotracheal tube 34. The outside surface of the coaxial nipple 48 has a slightly larger diameter than the inside 45 of the end portion 42 of the endotracheal tube 34 so that a press fit is formed. According to FIG. 3, an outwardly-projecting bead 49 is coaxially on the left of the nipple 48 without changing its inside diameter. The bead 49 tightly engages an end face 52 of the end portion 42 of the endotracheal tube 34 and has exactly the same outside diameter so that a smooth, step-less transition is formed to facilitate introduction into the conventional endotracheal tube 19 (FIGS. 1 and 2). On the leftward side of the bead 49, remote from the end portion 42 of the endotracheal tube 34, the casing 47 has a coaxial right-cylindrical recess 54. A socket recess 56 extends annularly thereabout.

A cup-shaped, stainless steel cap 57 which is substantially rotationally symmetric has, between its end face 58 and its cylindric, open end 59, rounded surfaces 61 of relatively great radius. The cylindric, open end 59 of the cap 57 coaxially overlaps the annular socket 56 of the casing 47 as far as the bead 49 with which it is circumferentially flush, so that there is no stepped transition here, either. The open end 59 of the cap 57 is permanently joined to the annular socket 56, either by cementing or by press-fitting. The end face 58 of the cap is relatively thick with a blind hole 66 bored from and coaxial with its inside surface 64. The inside surface 64 is coaxial with and precisely radial of the longitudinal axis 67 of the end portion 42 of the endotracheal tube 34. A cylindric circumferential surface 68 which continues steplessly into the cylindric recess 54 stands perpendicular to and coaxial with the inside surface 64.

Figures 4, 6:
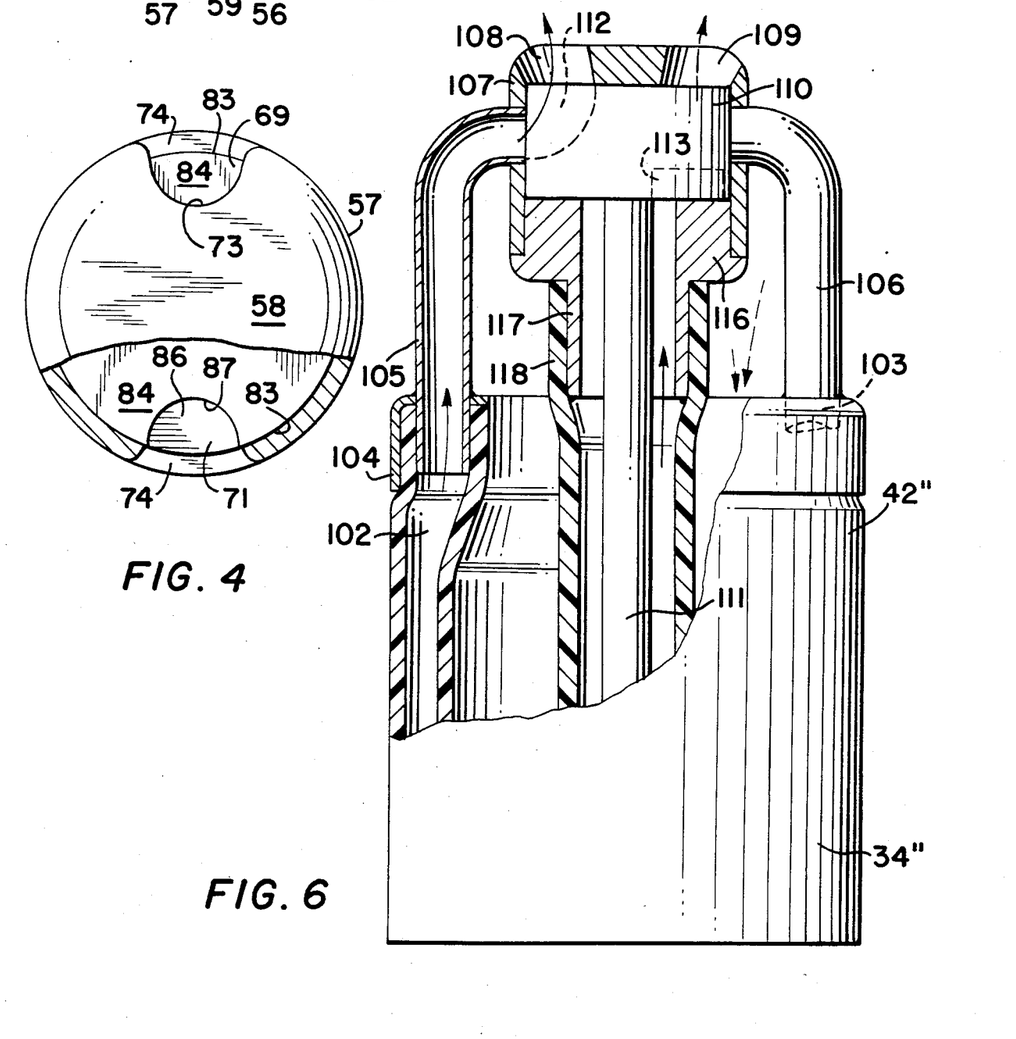
FIG. 4 is an end view of the portion of the embodiment shown in FIG. 3.
FIG. 6 is a longitudinal front elevation of an end portion of still another embodiment, partly broken away and in section.

Two discharge ports 69 and 71 are offset 180° from one another in the peripheral rounded surfaces 61 of the cap 57. A mark 69a along the endotracheal tube externally indicates their position when inserted in the trachea. The discharge ports 69 and 71 have inner apexes 73 and outer apexes 74, the apexes 73 lying in the bottom 63 and the apexes 74 in the circumferential wall 72.

A terminal 76 holds the end of the flexible shaft 43 at the end portion 42 of the endotracheal tube 34 for coaxial rotation therewith. On the coaxial terminal 76 are vanes 77 of such an angle relative to the direction of rotation of the flexible shaft as to force the artificial respiration air supplied to the endotracheal tube 34 leftwardly as shown in FIG. 3. After a radial step 78, the terminal 76 merges into one end of a cylindrical, coaxial pin 79, the other end of which is carried rotatably in the blind hole 66 of the end face of the cap. Onto the pin 79, there is press-fitted for co-rotation a rotor 81 which engages the cylindric recess 54 rotatably, but in a fairly air-tight manner which also provides an abutment for any linear movements of the rotor 81 and the connected shaft 43. The cylindric circumference 83 of the rotor 81 is also guided rotatably by the circumferential surface 68 of the cap which is flush with the cylindric recess 54 so that the radial movements exceeding the rotational free play are not possible and a certain air-tightness is achieved. As can be seen in FIG. 3, the circumference 83 of the rotor reaches into the discharge ports 69 and 71 without extending beyond them. Parallel to the annular face 82 there is provided on the left an annular face 84 of the same size, which likewise extends partially into the discharge ports 69 and 71, but otherwise is guided by the inside surface 64.

In the rotor 81 is an outlet orifice 86 running outwardly at an acute angle to the axis 67. The inside 87 of the orifice 86 leads from the circumference of the terminal 76 to the apex 73 so that, in this direction, the discharge opening 86 has maximum size. The discharge opening 86 is also maximal in the other direction because its outside 88 runs from the inside circumference of the bead 49 to the apex 74. The discharge opening 86 also opens funnel-wise toward end face 58 which, together its outward angle, functions in conjunction with the rotational energy imparted by the rotor to actively pull artificial respiration air therethrough. The rotation of the discharge opening 86 to the discharge ports 69 and 71 makes pulses from this.

According to FIG. 5, the base 91 of a resilient rubber, molded, Y-shaped, tubular divider 92 is slipped onto the cap 57' of the rotary slide valve described with reference to FIGS. 1 to 6. One leg 93 thereof aims its orifice 94 into one trunk bronchus TB at the more-obtuse angle thereof and the other leg 96 of the divider 92 aims its orifice 97 into the other trunk bronchus TB at the more acute angle thereof. The legs 93 and 96 are substantially smaller in outside diameter than the inside diameter of the trunk bronchi, however, so that very adequate room is left for the return of waste artificial respiration air. The discharge ports 69 and 71 aim in the right direction, along legs 93, 96, if the base 91 has been correctly attached, as shown.

When this artificial respiration apparatus is introduced, the resilient tubular divider 92 that is on the rotary valve will, after rather delicate insertion and turning, therefore, fit anatomically and functionally correctly into the trachea and bronchi. The mark 69a' shows, on the one hand, that the apparatus is correctly seated in this way and, on the other hand, prevents accidental turning in operation.

Figures 7, 8:
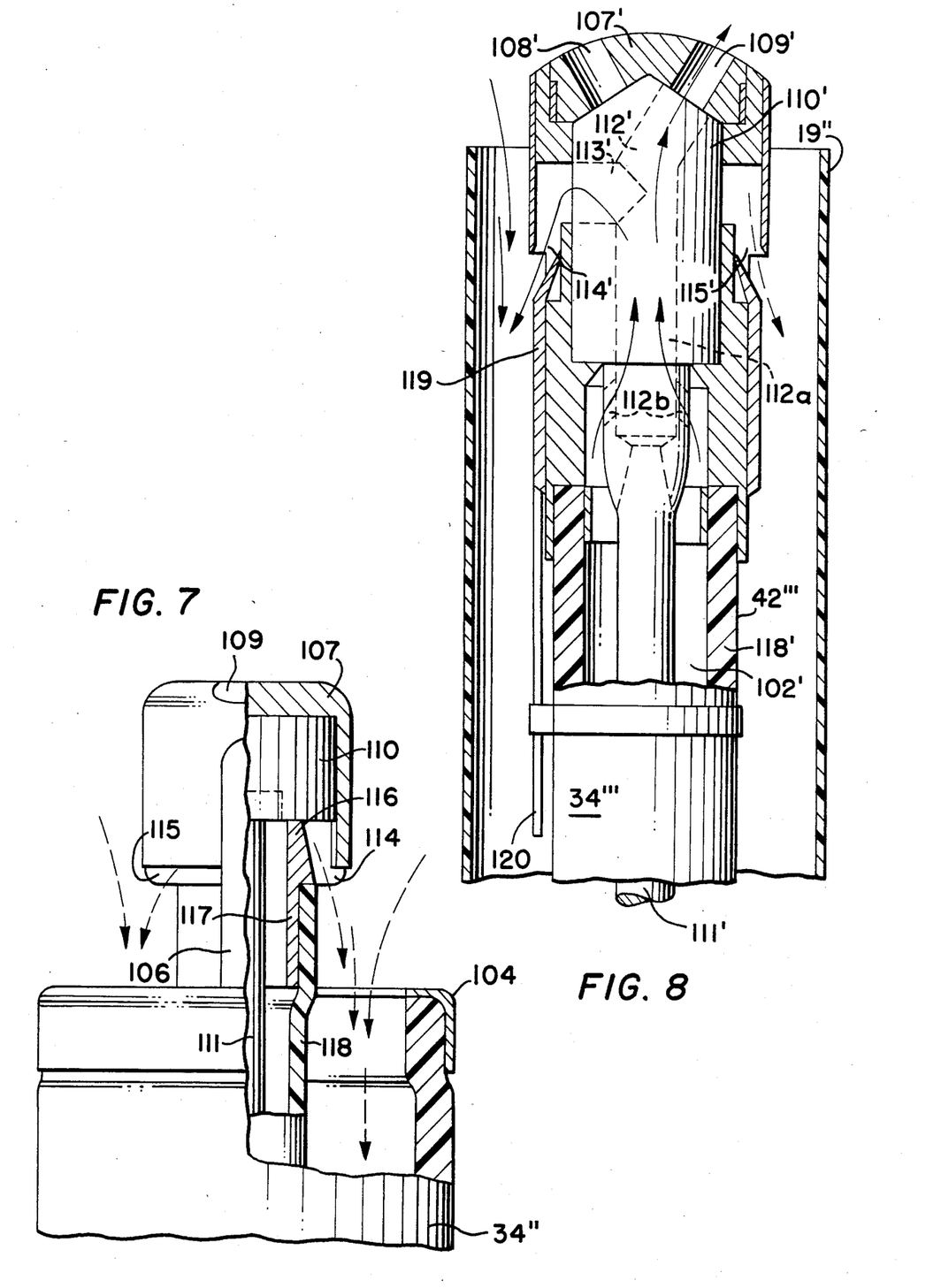
FIG. 7 is a longitudinal side elevation of the end portion of the embodiment shown in FIG. 6, partly broken away and in section.
FIG. 8 is a longitudinal front elevation of an end portion of still another embodiment, partly in section.

In FIGS. 6 and 7, there is shown an embodiment of an oscillating respirator. Its endotracheal tube 34" is similar to tube 19 already described with respect to FIGS. 1 to 4, but modified in that it contains two air-supply passages 102 and 103 let into its wall in addition to the already-mentioned passages (24, 29, FIG. 2) for the aspiration of secretions and the compressed air supply for a sealing balloon. The end 42" of this endotracheal tube is gripped by a ring 104 which is pressed and cemented onto it. The ring is shaped such that the outside dimensions of the endotracheal tube 34" are substantially preserved.

The ring is such that one end of each of two, thin-walled tubes 105 and 106 let through the ring extend into the air supply passages 102 and 103 integrated into the endotracheal-tube wall for supplying respiration air as later described. The supply passages are thereby expanded thereabout, thus creating a tight and leak-proof seating. In addition, these connections are also cemented.

At their other ends, the tubes 105 and 106 are bent 90° and extend into a cap 107 to which they are permanently attached. In the cap, two discharge ports 108 and 109 are provided offset from one another by 180° and symmetrically spaced from the center line.

A rotor 110 is inside the upper part of the cap 107. The rotor is connected fixedly to a flexible shaft 111 by which it can be rotated.

Two grooves 112, 113 are cut into the rotor. Groove 112 operatively connects the lungward discharge ports 108 and 109 respectively to the air supply of tubes 105, 106 as the rotor rotates the groove thereto. The other groove 113 operatively connects oppositely, mouth-ward-aimed ejector or reverse blast ports 114 and 115 (FIG. 7) for producing a suction in the mouth of the ring 104 as the rotor rotates the groove thereto. The mouthward-aimed ejector ports 114 and 115 are in a cylindric body 116 which extends from the bottom of the cap, opposite the discharge portions 108, 109, is permanently attached thereto and forms, together with the cap, a bearing for the rotor. The cylindric body 116 has a tubular prolongation 117 over which a hose 118 lying centrally in the endotracheal tube 34" is slipped. The hose is thus expanded for a pressure-resistant connection which is also cemented. The hose 118 has two functions: it serves for guiding the flexible shaft 111 and it serves as an air feed line for the mouthwardly-aimed reverse blast openings 114, 115. The air stream emerging from the discharge ports 108 and 109 can therefore be varied from the outside independently of the air stream issuing from the reverse blast openings 114 and 115.

The embodiment of FIG. 8 is similar in operation to that of FIGS. 6 and 7 described above. The valve in this case, too, is a rotary slide valve, its rotor 110' being driven by the flexible shaft 111'. In contrast to the embodiment of FIGS. 6 and 7 described above, however, only one supply line 102' is provided by the space between the flexible shaft 111' and the endotracheal tube 34''' which, therefore, also corresponds to the previously-described hose line 118'; surrounding the shaft at a distance therefrom. The hose line 118' thus simultaneously forms the artificial respiration air-supply line and the supply line for the mouthward-aimed ejector or reverse blast ports 114', 115'. It is affixed at the upper end of the stator or cap 107'. The rotor 110' is relatively rotatable in the cap 107'.

The interior 112a of the rotor 110, is in constant communication with the interior 102' of the artificial respiration air line 118', i.e. endotracheal tube 34''', through lateral openings 112b. The compressed air fed through the artificial respiration air line, i.e. endotracheal tube 34''' passes from the interior 112a of the rotor in the direction of the lungs through the groove 112' and discharge ports 108' and 109' and in the direction of the mouth through the groove 113' and reverse blast ports 114', 115' formed by annular gap segments in the cap 107' depending on the position of the rotor. Thus, in this embodiment, respiratory-air pulses are supplied to the lungs and used breathing air is aspirated from the air cells of the lungs and carried through the conventional endotracheal tube 19" into the open air simultaneously.

The cross sections of the return-air ports 114, 115 formed by the annular gap flow cross section segments are variable throttled by axial displacement of an adjusting cone 119 thereat. Axial displacement of the adjusting cone 119 can be performed from the outside by means of the adjuster rod 120 extending along the endotracheal tube 34'''. The ratio between the air volume fed in and withdrawn with each breathing cycle can thus be adjusted as desired with great reliability of operation, which is an outstanding advantage.

Figure 9:
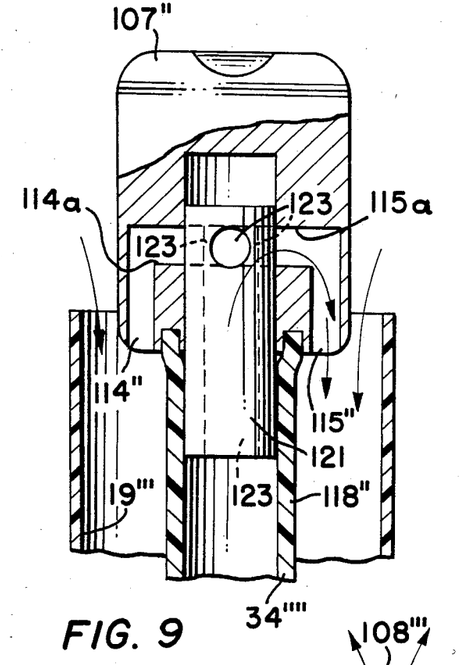
FIG. 9 is a longitudinal side elevation of an end portion of still another embodiment, partly in section.
Figure 10:
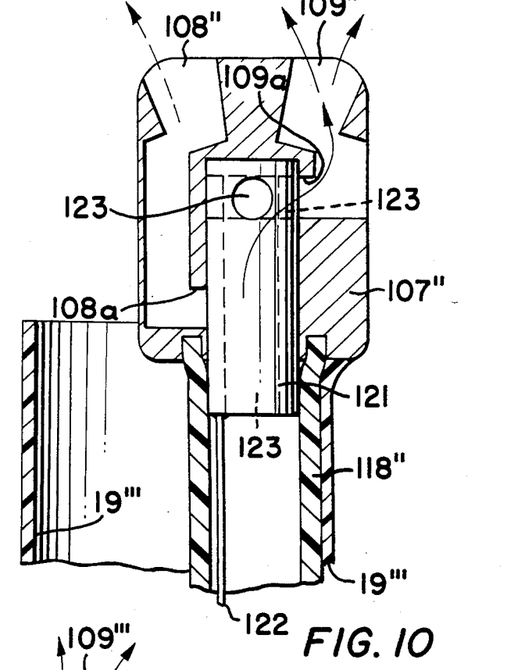
FIG. 10 is a longitudinal front elevation of the end portion of the embodiment shown in FIG. 9, partly in section.

FIGS. 9 and 10 relate to a simplified embodiment in which a flat or axially-operated slide valve is employed. Its valve body 121 is mounted in the artificial respiration air supply line 118''' i.e. endotracheal tube 34''', which is closed at the top, outlet end by a cap 107". The valve body 121 is axially displaceable by an adjuster rod 122 to bring a cross-ended passage 123 into alignment alternately with axially-spaced ports 108a, 109a associated respectively with the discharge ports 108" and 109" or with aligned ports 114a, 115a associated respectively with the reverse blast discharge ports 114", 115" axially therebetween. The air volume fed through the artificial respiration air line 118" is thus alternately delivered into the lung as fresh respiratory-air pulses or used for exhausting used breathing air into the interior of the endotracheal tube 19''' and through the latter into the open air. The eccentric association of the artificial respiration air line 118" with the endotracheal tube 19''' is explained by FIG. 10.

Figure 11:
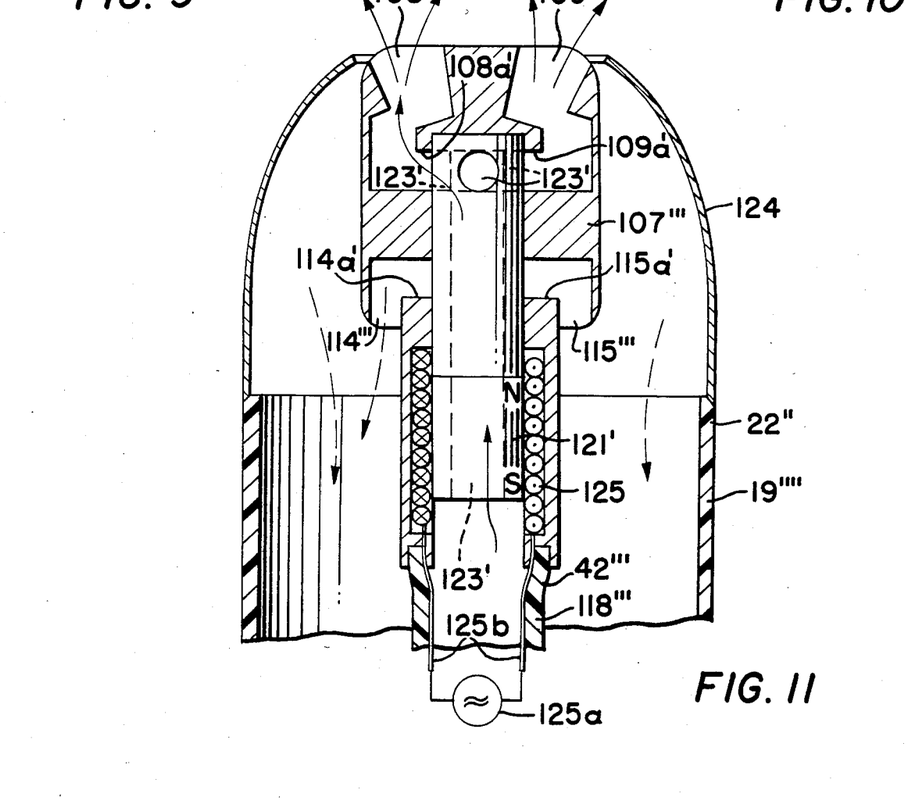
FIG. 11 is a longitudinal front elevation of an end portion of still another embodiment, partly in section.

The embodiment shown in FIG. 11 is functionally similar to that of FIGS. 9 and 10 described above. For axially displacing the valve body 121' of the flat slide valve, however, there is provided, in this case, an electromagnetic drive. The end 22" of the endotracheal tube 19''' is also covered, only substantially, by a domed structure 124 to facilitate insertion into the trachea.

The valve body 121' is a magnet provided with a surface coating (not shown) of nonconducting plastic for the prevention of galvanic or electrical interactions. It is axially displaceable in a guiding electromagnet-coil sleeve 125 on the end 42''' of the endotracheal tube or artificial respiration air line 118''' by the action of the electromagnetic forces of the coil therein. Its passage 123' steers the fresh air fed from the artificial respiration air line alternately in the direction of the discharge ports 108''' and 109''' or in the direction of the return-air ports 114''', 115''', according to the direction of the magnetic field produced by coil-connected source 125a. In the former case, fresh air is fed into the lung, and in the latter case waste breathing air is withdrawn from the lung using entrainment effect. The switching, respiratory-air pulse frequencies that can be achieved are considerable to permit a wide range of therapeutic applications. Vibrations are kept very much away from the patient, and introduction into the trachea becomes easier if the wires are 125b for the delivery of the electric power from the source 125a to the electromagnetic-coil sleeve 125 are more flexible than the shafts in the mechanical variants described above. High accuracy of response is an additional advantage to be emphasized.

What is claimed is:

1. Apparatus for producing high-frequency, respiratory-air pulses for artificial respiration, comprising:

a flexible endotracheal tube having a proximal end adapted to extend from a breathing passage of a patient and a distal end adapted to extend into the trachea of a patient, which distal end defines an outlet;

valve means mounted in the outlet of the endotracheal tube and having an inlet communicating with the interior of the endotrachael tube and outlet means for directing respiratory-air pulses into the trachea of a patient; and respiratory air supply means connected to the proximal end of the endotracheal tube for supplying respiratory air to the valve means outlet and control means along the end endotracheal tube for operating the valve means to produce said pulses of the supplied respiratory air.

2. Apparatus according to claim 1, wherein the valve means and control neans are mechanical.

3. Apparatus according to claim 2, wherein the valve means is a rotary slide valve.

4. Apparatus according to claim 3, wherein the control means comprises a rotatable, flexible shaft extending along the endotracheal tube to the rotary slide valve and the rotary slide valve comprises a rotor coaxially joined to the shaft.

5. Apparatus according to claim 3, wherein the rotary slide valve further comprises blades mounted on the shaft adjacent the valve inlet for raising the pressure of the respiratory air from the supply means to the valve inlet.

6. Apparatus according to claim 3, wherein the rotary slide valve comprises a rotor having at least one opening communicating with the valve inlet and a stator having at least more than one opening communicating with the outlet means, the opening in each the rotor and stator being alignable such that when the rotor is rotated, the openings are intermittently aligned to produce the respiratory-air pulses.

7. Apparatus according to claim 6, wherein said endotracheal tube is curved and the stator has two exit openings offset by 180° from one another and in the plane of curvature of the endotracheal tube.

8. Apparatus according to claim 7, and further comprising a mark indicating the position of the exit openings extending over the entire length of the endotracheal tube.

9. Apparatus according to claim 3, wherein the rotary slide valve comprises a rotor axially enveloped by a stator such that the rotor nowhere projects beyond the circumference of the stator.

10. Apparatus according to claim 2, wherein the valve means is a flat slide valve.

11. Apparatus according to claim 1, wherein the valve means and control means are electrical.

12. Apparatus according to claim 1, and further comprising, in combination, a conventional endotracheal tube surrounding the endotracheal tube to act as a sleeve therearound.

13. Apparatus according to claim 12, wherein the conventional endotracheal tube is spaced from the inner endotracheal tube for forming a return air line therebetween.

14. Apparatus according to claim 12, wherein the endotracheal tube are coaxial of each other.

15. Apparatus according to claim 12, wherein the endotracheal tubes eccentric of each other.

16. Apparatus according to claim 12, and further comprising at least one passage in the wall of the conventional endotracheal tube for providing flow communication between the proximal and distal end portions thereof.

17. Apparatus according to claim 1, and further comprising pressure-raising means in the endotracheal tube adjacent the valve means for raising the pressure of the respiratory air from the supply means to the valve inlet.

18. Apparatus according to claim 17, wherein the pressure-raising means comprises an air-turbine apparatus actuated by the control means.

19. Apparatus according to claim 18, wherein the valve means is a rotary slide valve and the control means comprises a single flexible shaft for driving the rotary slide valve and the air-turbine apparatus.

20. Apparatus according to claim 1, and further comprising a Y-shaped, rubber tubular divider having the base of the Y shape mounted on the outlet of said valve means, whereby the two branches of the Y shape of the divider run at an acute angle to the endotracheal tube corresponding to the configuration of trunk bronchi.

21. Apparatus according to claim 1, and wherein the outlet means further comprises at least one direct blast opening and at least one reverse blast opening from the valve means, the direct blast opening being directed away from the distal end of the endotracheal tube into the trachea and the reverse blast opening being directed back toward the proximal end of the endotracheal tube.

22. Apparatus according to claim 21, wherein the valve means directs air from the supply means to flow through the direct blast opening and the reverse blast opening alternately.

23. Apparatus according to claim 21, wherein the valve further comprises throttling means for at least one of the direct blast openings and the reverse blast opening.

24. Apparatus according to claim 23, and further comprising means along the endotracheal tube for operating the throttling means, whereby the ratio of the air flows through the direct blast opening and the reverse blast opening is variable.

* * * * *